US00PP37402P2

(12) United States Plant Patent
O'Connell

(10) Patent No.: US PP37,402 P2
(45) Date of Patent: Apr. 28, 2026

(54) ***PORTULACARIA* PLANT NAMED 'Jubilee'**

(50) Latin Name: *Portulacaria afra*
Varietal Denomination: Jubilee

(71) Applicant: Altman Specialty Plants llc, Vista, CA (US)

(72) Inventor: Renee O'Connell, Pala, CA (US)

(73) Assignee: Altman Specialty Plants llc, Vista, CA (US)

( * ) Notice: Subject to any disclaimer, the term of this patent is extended or adjusted under 35 U.S.C. 154(b) by 0 days.

(21) Appl. No.: 19/264,378

(22) Filed: Jul. 9, 2025

(51) Int. Cl.
*A01H 5/02* (2018.01)
*A01H 6/00* (2018.01)

(52) U.S. Cl.
USPC ..... Plt./471
CPC ..... *A01H 6/00* (2018.05)

(58) Field of Classification Search
USPC ..... Plt./471
CPC ..... A01H 5/02; A01H 5/12
See application file for complete search history.

*Primary Examiner* — Kent L Bell

(57) ABSTRACT

A new and distinct cultivar of *Portulacaria afra* plant named 'Jubilee' is disclosed, characterized by green and yellow foliage with a gold hue. Plants are upright with slightly lax, non-brittle stems. Due to the obvious gold hue of *Portulacaria afra* 'Jubilee', this plant is particularly useful in mixed plantings on the patio or where a gold hue is desired in decor. *Portulacaria afra* 'Jubilee' begins to offset at an early age; resulting in a much-branched morphology at a smaller size, allowing for use in a multitude of pot sizes, from 2.5" to 8" or larger. The new cultivar is a *Portulacaria afra*, normally used for ornamental purposes.

1 Drawing Sheet

Latin name of the genus and species: *Portulacaria afra*.
Cultivar denomination: 'JUBILEE'.

BACKGROUND OF THE INVENTION

The new cultivar is a product of a naturally occurring whole plant mutation in a commercial nursery in Vista, California. The parent is the unpatented commercial variety *Portulacaria afra* 'Variegata'. 'JUBILEE' was found and selected by the inventor at a commercial greenhouse in Vista, California during May of 2021.

Asexual reproduction of the new cultivar 'JUBILEE' was first performed by vegetative tip cuttings at a commercial greenhouse in Vista, California in November of 2021. 'JUBILEE' has since produced at least 15 generations and has shown that the unique features of this cultivar are stable and reproduced true to type.

SUMMARY OF THE INVENTION

The cultivar 'JUBILEE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'JUBILEE'. These characteristics in combination distinguish 'JUBILEE' as a new and distinct *Portulacaria* cultivar:

1. The new cultivar *Portulacaria afra* 'Jubilee' forms an upright growth habit with slightly lax stems with green and yellow gold hued foliage.
2. Due to the obvious gold hue of *Portulacaria afra* 'Jubilee', this plant is particularly useful in mixed plantings on the patio or where a gold hue is desired in decor.

3. *Portulacaria afra* 'Jubilee' begins to offset at an early age; resulting in a much branched morphology at a smaller size, allowing for use in a multitude of pot sizes, from 2.5" to 8" or larger.

PARENTAL COMPARISON

Plants of the new cultivar 'JUBILEE' are similar to the parent in most horticultural characteristics. However, plants of the new cultivar differ from the parent in the following:

1. *Portulacaria afra* 'Jubilee' is a variegate with an enhanced gold hue, whereas the parent variety, *Portulacaria afra* 'Variegata' does not display the strong gold cast.
2. *Portulacaria afra* 'Jubilee', due to its more compact morphology, can be utilized for pot smaller pot sizes, whereas *Portulacaria afra* 'Variegata' is more suited for larger pots.

COMMERCIAL COMPARISON

'Jubilee' can be compared to the unpatented commercial cultivar *Portulacaria afra* 'Sunkissed' (co-pending U.S. Plant patent application Ser. No. 19/264,395). The two *Portulacaria* varieties are similar in most horticultural characteristics; however, the new cultivar differs in the following:

1. *Portulacaria afra* 'Jubilee' displays an enhanced gold hue, whereas *Portulacaria afra* 'Sunkissed' exhibits more of a white and green coloration, sometimes blushed pink.
2. *Portulacaria afra* 'Jubilee' displays a more upright morphology, whereas *Portulacaria afra* 'Sunkissed' exhibits a strongly cascading morphology, suitable for hanging baskets.

'Jubilee' can also be compared to the commercial cultivar *Portulacaria afra* 'Lilliput' U.S. Plant Pat. No. 32,011. The two *Portulacaria* varieties are similar in most horticultural characteristics; however, the new cultivar differs in the following:

1. *Portulacaria afra* 'Jubilee' exhibits variegated leaves with a strong gold hue, whereas the leaves of *Portulacaria afra* 'Lilliput' U.S. Plant Pat. No. 32,011 are solid green, without variegation.
2. *Portulacaria afra* 'Jubilee' produces larger leaves, whereas *Portulacaria afra* 'Lilliput' U.S. Plant Pat. No. 32,011 produces very petite leaves.
3. *Portulacaria afra* 'Jubilee' is a faster grower than is *Portulacaria afra* 'Lilliput' U.S. Plant Pat. No. 32,011.

BRIEF DESCRIPTION OF THE PHOTOGRAPH

The photograph was taken using conventional techniques and equipment. While the colors in the photograph may display variances of color as compared to the living cultivar, due to LRV (light reflectance value), they are as accurate as possible using conventional photographic techniques. Colors in the photograph may appear to differ slightly from the color values cited in the botanical description, which accurately describe the colors of new *Portulacaria afra* 'Jubilee'. The included figure is a photograph of a typical plant of 'Jubilee' at 5 months of age from a rooted cutting. The plant was grown in a greenhouse in Vista, CA. (approximately 2500 to 3000 foot candles). Temperatures ranged from approximately 34 F to 90 F.

DETAILED BOTANICAL DESCRIPTION

In the following description, color references are made to The Royal Horticultural Society Color Chart, 2015 edition, except where general terms of ordinary dictionary significance are used. The following observations and measurements describe 'JUBILEE' plants in a commercial shadehouse in Vista, California. Temperatures ranged from 34° F. to 90° F. during the night and day. No artificial light, photoperiodic treatments or chemical treatments were given to the plants. Natural light conditions were approximately 2500 to 3000 foot candles of light. Measurements and numerical values represent averages of typical plant types.
Botanical classification: *Portulacaria afra* 'JUBILEE'.
Age of the plant described: About 5 months.

PROPAGATION

Time to initiate roots: Approximately 25 days at 22° C.
Propagation method: Vegetative tip cuttings.

PLANT

Growth habit: Tender succulent. Upright, with lateral branches occurring at angles of 15 to 85° from center. 45° angles most common.
Container size: 5-inch.
Height: Approximately 22 to 25 cm.
Plant spread: Approximately 30 cm, in a 5-inch pot.
Branching characteristics: Opposite.
Length of lateral branches: Average range 7 to 12 cm.
Diameter of lateral branches: Approximately 6 to 9 mm.
Quantity branches: 2 to 4 large main lateral branches, from each main stem. Upper section of main stems has 6 to 10 small lateral branches forming.
*Texture*.—Glabrous.
*Shape*.—Round.
*Color*.—Immature: Greyed-Purple N186D. Mature: Greyed-Purple 185C with layer of N187C and N187D.
Root description: Densely fibrous. Grey-Brown N199A and N199B.

FOLIAGE

Leaf:
*Arrangement*.—Opposite.
*Average length*.—Average range 1.5 to 1.9 cm.
*Average width*.—1.5 cm.
*Shape of blade*.—Broad obovate to broad spatulate.
*Apex*.—Broad rounded, mucronate.
*Base*.—Broad taper.
*Margin*.—Entire.
*Texture of top surface*.—Glabrous.
*Texture of bottom surface*.—Glabrous.
*Appearance of top surface*.—Slightly glossy.
*Appearance of lower surface*.—Slightly glossy.
*Quantity of leaves per branch*.—Approximately 40 to 60.
*Color*.—Young foliage upper side: Center section Green 143A and 143C. Large marginal coloration Yellow 2C. Young foliage, under side: Center section Green 138A and 138B Large marginal coloration Yellow 2C. Mature foliage upper side: Center section Green 143A and 143C. Large marginal coloration Yellow 2C. Overall Yellow 2D hue. Mature foliage, under side: Center section Green 143A and 143C. Large marginal coloration Yellow 2C. Overall Yellow 2D hue.
*Venation*.—There is no visual appearance of venation.

FLOWER

Flowering not observed.

OTHER CHARACTERISTICS

Fruits and seeds: Not observed to date.
Temperature tolerance: USDA zones 10 and above.
Disease/pest resistance: Neither resistance nor susceptibility to pathogens or pests of *Portulacaria* observed.
Drought tolerance: Tolerant to drought.

What is claimed is:

1. A new and distinct cultivar of *Portulacaria afra* plant named 'Jubilee' as herein illustrated and described.

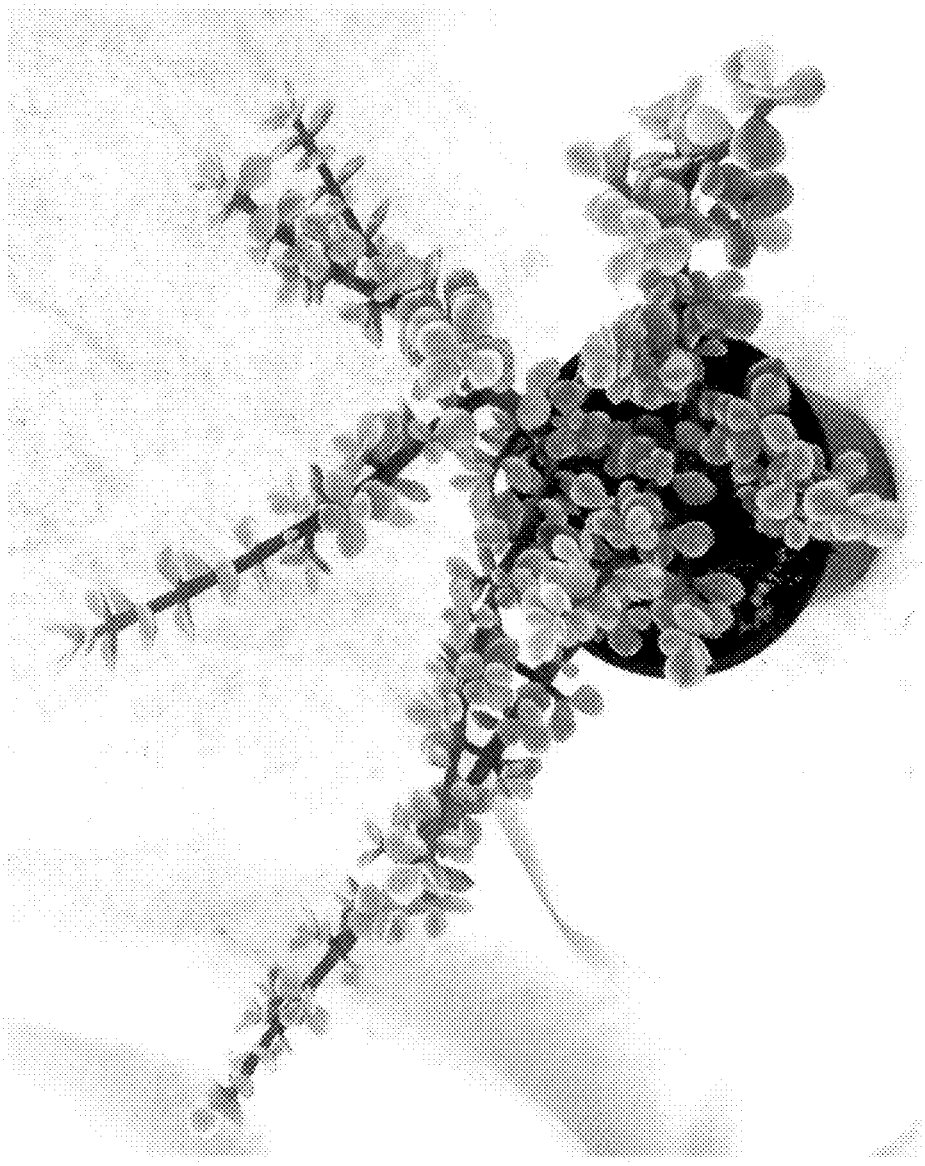

* * * * *